United States Patent [19]

Uram

[11] Patent Number: 5,893,828
[45] Date of Patent: Apr. 13, 1999

[54] CONTACT LASER SURGICAL ENDOSCOPE AND ASSOCIATED MYRINGOTOMY PROCEDURE

[76] Inventor: Martin Uram, 39 Sycamore Ave., Little Silver, N.J. 07739

[21] Appl. No.: 08/640,542

[22] Filed: May 2, 1996

[51] Int. Cl.⁶ .................................................. A61B 1/227
[52] U.S. Cl. ........................... 600/108; 600/182; 606/15; 607/92
[58] Field of Search ....................... 600/104, 105, 600/108, 182, 117; 606/13–16, 109; 607/88, 89, 92, 93

[56] References Cited

U.S. PATENT DOCUMENTS

| | | | |
|---|---|---|---|
| 3,858,577 | 1/1975 | Bass et al. ......................... | 600/108 |
| 4,604,992 | 8/1986 | Sato ................................... | 600/108 |
| 4,607,622 | 8/1986 | Fritch et al. . | |
| 4,693,244 | 9/1987 | Daikuzono ........................ | 606/16 |
| 4,712,537 | 12/1987 | Pender .............................. | 606/109 |
| 4,987,884 | 1/1991 | Nishioka et al. ................. | 600/108 |
| 5,051,823 | 9/1991 | Cooper et al. .................... | 600/108 |
| 5,121,740 | 6/1992 | Uram . | |
| 5,280,378 | 1/1994 | Lombardo ......................... | 606/18 |
| 5,313,962 | 5/1994 | Obenchain ........................ | 606/14 |
| 5,498,258 | 3/1996 | Hakky et al. ..................... | 606/15 |
| 5,700,236 | 12/1997 | Sauer et al. ...................... | 600/175 |

*Primary Examiner*—John P. Leubecker
*Attorney, Agent, or Firm*—McAulay Nissen Goldberg Kiel & Hand, LLP

[57] ABSTRACT

In a myringotomy, a selected amount of tympanic membrane tissues are removed from a patient by the application of laser energy to vaporize the tissues. An endoscope is inserted into the ear canal and used to visually detect and locate the cellular material to be removed. The endoscope has a laser guide with a distal tip which extends beyond the distal end of the optical elements of the endoscope, thereby enabling placement, under direct visual observation, of the distal tip of the laser guide in contact with the tympanic membrane. A controlled amount of electromagnetic radiation is transmitted along the laser guide only after contact of the distal tip of the laser guide with the tissues to be removed.

4 Claims, 1 Drawing Sheet

CONTACT LASER SURGICAL ENDOSCOPE AND ASSOCIATED MYRINGOTOMY PROCEDURE

BACKGROUND OF THE INVENTION

This invention relates to a myringotomy operation and to an associated instrument.

Children frequently have an abnormal condition characterized by fluid in the middle ear cleft. In a myringotomy or tympanotomy operation, a surgical incision is made with a cutting blade in the tympanic membrane or the patient to allow the release of trapped fluid. Generally, a ventilation or pressure equalization tube is placed in the incision to drain the fluid and ventilate the middle ear for a longer period than would be possible with only an incision of the ear drum. A myringotomy and tube placement is conventionally performed in a hospital operating room. This is an expensive procedure, owing to the necessary presence of several specialists (anesthesiologist, surgeon, etc.).

It is known to use a carbon dioxide laser to burn a hole in the tympanic membrane. This procedure is expensive, inasmuch as it requires expensive laser equipment and an expensive microscope. Moreover, the procedure produces an aperture of two millimeters in the tympanic membrane, which is too large to be useful for most myringotomies.

OBJECT OF THE INVENTION

An object of the present invention is to provide an improved method for use in draining fluid from the middle ear.

Another object of the present invention is to provide such a method which may be performed in the doctor's office and does not require anesthesia.

Yet another object of the present invention is to provide such a method which is inexpensive and easy to perform.

An additional object of the present invention is to provide an instrument for carrying out the method.

These and other objects of the present invention will be apparent from the descriptions and illustrations herein.

BRIEF DESCRIPTION

In accordance with a particular embodiment of the present invention, a selected amount of internal tissues are removed from a patient by the application of laser energy to vaporize the unwanted material. More particularly, an endoscope is used to visually detect and locate the material to be removed. The endoscope has a laser guide with a distal tip which extends beyond the distal end of the optical elements of the endoscope, thereby enabling placement, under direct visual observation, of the distal tip of the laser guide in contact with the tissues to be removed. A controlled amount of electromagnetic radiation is transmitted along the laser guide only after contact of the distal tip of the laser guide with the tissues to be removed.

This procedure is particularly beneficial in myringotomy operations. The formation of an aperture in the tympanic membrane can be performed quickly, with a minimum of discomfort to the patient. For this reason, the patient need not be placed under anesthesia. Accordingly, the procedure may be performed in the doctor's office, rather than a hospital operating room. The cost reduction over the conventional surgical procedure are substantial.

The instrument, with a fixed laser guide extending a pre-established distance beyond the optical elements, enables the performance of a minimally invasive procedure wherein a discrete, fixed amount of cellular and/or inorganic material is eliminated from a precisely determined location in a patient's ear canal, specifically at the tympanic membrane. The visual inspection of the surgical site before and during the operation, as well as the fixed location of the laser guide tip relative to the endoscope optics facilitates precision in the operation. The fixed extension of the laser guide is advantageous in providing a fixed and known standard length for estimating distances seen via the endoscope optics. The distal tip of the laser guide thus provides a reference point which enables a user to quickly and efficiently determine distances in the small area within the visual field of the endoscope optics.

Another advantage of the fixed attachment of the laser guide, as well as the optical elements, to the outer sleeve or tubular member of the endoscope is in facilitating sterilization of the instrument. Many endoscopes are provided with a so-called biopsy channel for the insertion of instruments during an endoscopic procedure. Such endoscope channels are notoriously difficult to clean and sterilize owing to their small diameter. The instant invention does not use a channel. Accordingly, a high degree of cleanliness is readily attainable.

In performing a myringotomy with a laser endoscope as disclosed herein, a hole as small as 100 microns across can be made in seconds. This is particularly beneficial where the patient is a child who will not remain still for a prolonged period.

DESCRIPTION OF THE PREFERRED EMBODIMENTS

Figure 1:
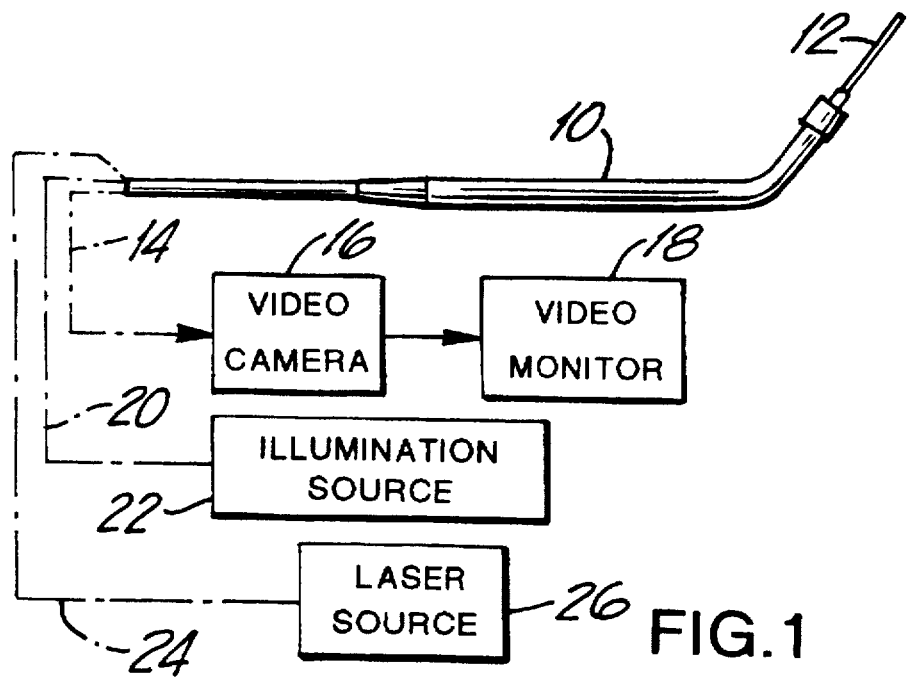
FIG. 1 is partially a side elevational view, on a reduced scale, and partially a block diagram of a video endoscope in accordance with the present invention.

As illustrated in the drawings, one embodiment of the endoscope of this invention has a handpiece 10 from which a probe 12 extends in a distal direction. Probe 12 is connected via a first cable 14 and a video camera 16 to a video monitor 18. A second cable 20 links probe 12 to a source 22 of illumination, while a third cable 24 is connected to a source 26 of laser energy.

Probe 12 comprises an outer sleeve or tubular casing member 28 (FIG. 2) which surrounds an illumination guide 30 including a large number of quartz optical fibers (not separately illustrated) which carry radiant energy from illumination source 22 through cable 20 towards a distal end 32 of probe 12. Embedded in illumination guide 30 are an image guide 34 and a laser guide 36. Image guide 34 includes a plurality of quartz optical fibers 38 which extend through cable 14 for transmitting an image from the distal end 32 of probe 12 to video camera 16. Laser guide 36 is a single optical fiber which longitudinally traverses cable 24 to transmit coherent monochromatic electromagnetic radiation or laser energy from source 26 to selected tissues of a tympanic membrane TM. To that end, an end 42 of laser guide 36 extends a predetermined, fixed distance d1 beyond distal end 32 of probe 12. More specifically, laser guide 36 terminates in a distal plane P1 spaced distance d1 from a plane P2 defined by distal end 32. Illumination guide 30 and image guide 34 essentially terminate in plane P2. Image guide 34 includes a lens 40 for focusing incoming light energy on distal ends of optical fibers 38.

Figure 2:
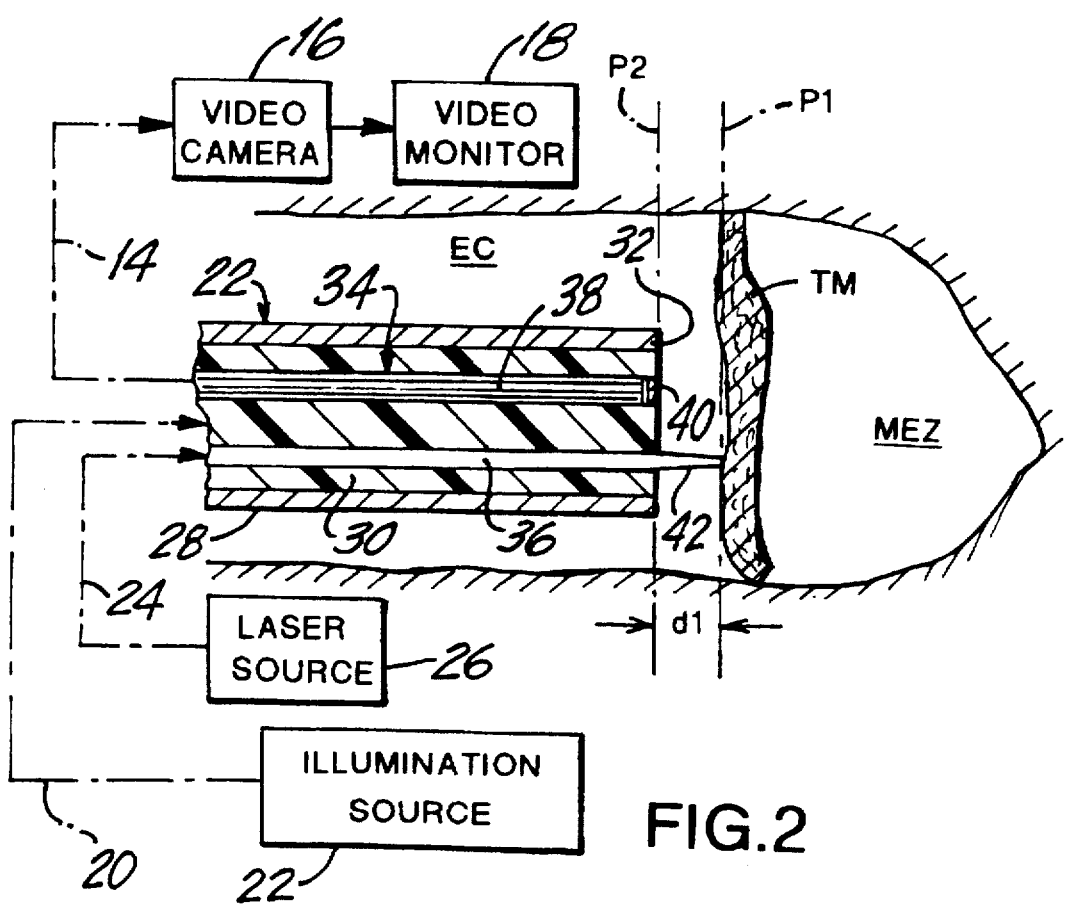
FIG. 2 is partially a schematic longitudinal cross-sectional view, on an enlarged scale, and partially a block diagram of the endoscope of FIG. 1, showing a distal tip of a laser guide in contact with a tympanic membrane of a patient.

In using the endoscope of FIG. 1, handpiece 10 is manipulated to insert a distal end portion of probe 12 into an ear canal EC of a patient, as shown in FIG. 2. During and after insertion of the distal end portion of probe 12 into the ear canal EC, illumination guide transmits radiant energy from source 22 to illuminate the tissues of the ear canal. Substantially simultaneously, image guide 34 carries pixels of light energy, in an ordered array forming an image, from lens 40 to camera 16. Camera 16 generates an electrical video signal which is applied to monitor 18 to display an image of the patient's ear canal tissues including tympanic membrane TM. During continued insertion of probe 12 into ear canal EC, the projecting distal tip of laser guide 36 provides a reference point facilitating the determination of distances and the relative locations of observed features. The distal tip of laser guide 36 is brought into contact with tympanic membrane TM, as shown in FIG. 2. At that juncture, and only then, is laser source 26 activated to generate coherent monochromatic electromagnetic radiation. The radiation is transmitted along laser guide 36 until the operator determines, through visual inspection of the real-time image on monitor 18, that tympanic membrane TM has been perforated to form an aperture (not shown) for releasing fluid from a middle ear region MEZ of the patient. The radiation transmission is terminated by actuating a switch (not shown), for example, via a foot pedal (not shown), to de-activate laser source 26. In a model of the laser endoscope described herein, laser source 26 produced electromagnetic energy in a continuous non-pulsed mode at a wavelength of 810 nm and at a power level of ½ to 1 ½ watt.

End 42 of laser guide 34 projecting from distal end 32 has a conical shape for increasing the power delivered to tympanic membrane TM during a myringotomy operation as described herein. Typically, conical end 42 has a length of 3.38 mm and tapers from a width of 600 microns to a width of 100 microns. In this case, probe 12 has a length of 1.57 inches or 39.94 mm.

It is to be noted that image guide 34, illumination guide 30 and laser guide 36 are sealed in tubular member 28 at least in a distal end portion thereof. Thus, bacteria and other infectious agents cannot be introduced into the instrument from one patient and subsequently transferred to another patient. The instrument of this invention is readily sterilizable, in contrast to endoscopes with a biopsy channel through which contaminated instruments are repeatedly passed.

The structure and composition of probe 12 is similar to that disclosed in U.S. Pat. No. 5,121,740. The disclosure of that patent is hereby incorporated by reference.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A surgical endoscope probe comprising:
   a tubular casing,
   an illumination guide, an optical image guide and a laser guide, each of said guides extending longitudinally through said tubular casing, said optical guide and said laser guide being embedded in said illumination guide,
   said illumination guide and said image guide each having a distal end at a first plane near the distal end of said tubular casing,
   said illumination guide, said image guide and said laser guide being fixedly sealed in said tubular casing,
   said laser guide having a distal end spaced distally by a predetermined fixed distance from said first plane.

2. The surgical probe of claim 1 wherein the portion of said laser guide that extends distally of said first plane is tapered from a greater diameter at said first plane to a lesser diameter at the distal tip of said laser guide.

3. The surgical probe of claim 1 wherein said optical, laser and illumination guides are the only elements in said tubular casing.

4. A surgical method comprising:
   providing an endoscope having an elongate tubular member with an illumination guide, a fiber-optic image guide and a laser guide, said laser guide having a distal tip extending a predetermined, fixed distance beyond a distal end of said image guide,
   inserting a distal end portion of said elongate tubular member into an ear canal of the patient,
   after said step of inserting said distal end portion of said elongate tubular member, viewing an image of a tympanic membrane of the patient, said image being transmitted via said image guide,
   placing said distal tip of said laser guide in contact with the viewed tympanic membrane of the patient, and
   only after placing of said distal tip of said laser guide in contact with the tympanic membrane, transmitting laser energy through said laser guide to vaporize and thus eliminate a selected portion of the membrane,
   forming an aperture of the tympanic membrane to permit release of fluid from a middle ear of the patient.

* * * * *